US012616219B2

(12) United States Patent
Sagalowicz et al.

(10) Patent No.: US 12,616,219 B2
(45) Date of Patent: May 5, 2026

(54) MILK ANALOGUE PRODUCT COMPRISING CEREAL AND LEGUME

(71) Applicant: SOCIETE DES PRODUITS NESTLE S.A., Vevey (CH)

(72) Inventors: Laurent Sagalowicz, Blonay (CH); Marianne Studer, Morrens (CH); Patricia Rossi Vauthey, Rivaz (CH); Elodie Audrey Soussan, Epalinges (CH); Laurence Sandoz, Echallens (CH); Cyril Moccand, Lully (CH); Klara Haas, Lausanne (CH); Evelien De Weert, Epalinges (CH)

(73) Assignee: Societe des Produits Nestle S.A., Vevey (CH)

( * ) Notice: Subject to any disclaimer, the term of this patent is extended or adjusted under 35 U.S.C. 154(b) by 578 days.

(21) Appl. No.: 18/002,559

(22) PCT Filed: Jun. 18, 2021

(86) PCT No.: PCT/EP2021/066657
§ 371 (c)(1),
(2) Date: Dec. 20, 2022

(87) PCT Pub. No.: WO2021/259802
PCT Pub. Date: Dec. 30, 2021

(65) Prior Publication Data
US 2023/0232850 A1     Jul. 27, 2023

(30) Foreign Application Priority Data

Jun. 24, 2020     (EP) ..................................... 20181846

(51) Int. Cl.
| | |
|---|---|
| *A23C 11/10* | (2025.01) |
| *A23G 1/48* | (2006.01) |
| *A23J 1/12* | (2006.01) |
| *A23J 1/14* | (2006.01) |
| *A23L 7/10* | (2016.01) |
| *A23L 11/00* | (2025.01) |
| *C12N 9/26* | (2006.01) |

(52) U.S. Cl.
CPC ................ *A23C 11/10* (2013.01); *A23G 1/48* (2013.01); *A23J 1/125* (2013.01); *A23J 1/148* (2013.01); *A23L 7/10* (2016.08); *A23L 11/05* (2016.08); *C12N 9/2414* (2013.01); *C12Y 302/01001* (2013.01)

(58) Field of Classification Search
None
See application file for complete search history.

(56) References Cited

FOREIGN PATENT DOCUMENTS

| | | | |
|---|---|---|---|
| CN | 104783172 | | 7/2015 |
| CN | 109497427 | A * | 3/2019 |
| CN | 110087489 | A | 8/2019 |
| CN | 110236064 | A | 9/2019 |
| JP | 2007097440 | A | 4/2007 |
| JP | 2007274944 | A | 10/2007 |
| WO | 2012029909 | A1 | 3/2012 |
| WO | 2013078510 | | 6/2013 |
| WO | 2016172570 | | 10/2016 |

OTHER PUBLICATIONS

Vogel, "How to make Sunflower Seed Milk", The Wayback Machine, Feb. 19, 2013, pp. 1-5.
"Water Lentil Milk: Parabel Achieves Dairy Alternative Breakthrough", Food Ingredients First, May 31, 2019, 4 pages.
"Qidian Seventh Revised Food Ingredient List", 2016, pp. 12.
Office Action Received for Application No. JP2022-577167, mailed on Nov. 5, 2024, 8 Pages (4 Pages of English Translation and 4 Pages of Official Copy).
Kishor et al., "Nutritional Composition of Chickpea (*Cicer arietinum*) Milk", International Journal of Chemical Studies, Volumen 05, Issue No. 04, 2017, pp. 1941-1944.

* cited by examiner

*Primary Examiner* — Jyoti Chawla
(74) *Attorney, Agent, or Firm* — K&L Gates LLP

(57) ABSTRACT

The present invention relates to a vegan food composition comprising at least 5 wt % cereal and at least 10 wt % legume on a dry basis, wherein said composition comprises at least 2 wt % dietary fiber provided by cereal and legume and at least 5 wt % protein provided by any one or more of said cereal and legume, and wherein the D4,3 particle size of said composition is less than 100 microns.

14 Claims, No Drawings

MILK ANALOGUE PRODUCT COMPRISING CEREAL AND LEGUME

CROSS REFERENCE TO RELATED APPLICATIONS

The present application is a National Stage of International Application No. PCT/EP2021/066657, filed on Jun. 18, 2021, which claims priority to European Patent Application No. 20181846.5, filed on Jun. 24, 2020, the entire contents of which are being incorporated herein by reference.

BACKGROUND OF THE INVENTION

Some consumers do not want to consume milk because of its animal origin, or because of lactose intolerance or dairy allergies. They may also see potential environmental sustainability issues.

Alternatives to milk do exist on the market. However, they often have several disadvantages in terms of composition and protein quality. They generally use protein extracts or isolates as source of protein, have a long list of ingredients, are not clean label (e.g. comprise gellan gum, hydrocolloids, and other additives), and the taste can be unpleasant, bitter and/or astringent.

The traditional means of producing a milk substitute uses acid or basic treatment. Filtration or centrifugation may be used to remove large particles, which creates grittiness and bitterness. As a result, the efficiency of the process is low and good nutrients like dietary fibers are removed. In addition, taste is often an issue and many ingredients are added to mask off-taste. Furthermore, many constituents like flavors and protein concentrates are often used in alternative plant milks and those have artificial and non-natural connotations for the consumer.

Most prior art vegan compositions use filtering to reduce particle size which has the disadvantage of removing dietary fiber and other beneficial components from the composition.

The dairy alternative market is growing by 11% each year and finding an alternative with good nutrition and taste will be a major advantage in this competitive field.

SUMMARY OF THE INVENTION

The present invention provides a vegan food composition which surprisingly preserves natural goodness and avoids grittiness without discarding any nutrients, particularly dietary fibers. In addition, it leads to short ingredient list using only natural ingredients.

Accordingly, the invention relates in general to a vegan food composition comprising cereal and legume.

The present invention provides a vegan food composition, preferably a liquid vegan food composition, comprising at least 3 wt % cereal on a dry basis, and at least 6 wt % legume on a dry basis, wherein said composition comprises at least 1 wt % dietary fiber provided by said cereal and legume and at least 5 wt % protein provided by any one or more of said cereal and legume.

In one embodiment, the vegan food composition comprises at least 5 wt % cereal on a dry basis, and at least 10 wt % legume on a dry basis, wherein said composition comprises at least 2 wt % dietary fiber provided by said cereal and legume and at least 5 wt % protein provided by any one or more of said cereal and legume.

In one embodiment, the vegan food composition comprises between 15 to 50 wt % cereal on a dry basis, and between 50 to 85 wt % legume on a dry basis, wherein said composition comprises between 5 to 20 wt % dietary fiber provided by said cereal and legume and between 5 to 40 wt % protein provided by any one or more of said cereal and legume.

In one embodiment, the vegan food composition is a liquid and the D4,3 particle size of said composition is less than 100 microns.

Preferably, the particle size is measured user laser diffraction.

In one embodiment, the vegan food composition further comprises oilseeds, preferably sunflower.

In one embodiment, the vegan food composition further comprises between 25 wt % to 50 wt % oilseeds on a dry basis, or about 35 wt % oilseeds on a dry basis.

In one embodiment, the vegan food composition is a powder.

In one embodiment, the vegan food composition is a liquid.

In one embodiment, the vegan food composition is a liquid having a viscosity of less than 100 mPa s as measured at 25° C. with apparatus at a shear rate of $100 \text{ s}^{-1}$, preferably less than 80 mPa s as measured at 25° C. with apparatus at a shear rate of $100 \text{ s}^{-1}$, preferably less than 50 mPa s as measured at 25° C. with apparatus at a shear rate of $100 \text{ s}^{-1}$.

In one embodiment, the vegan food composition is a liquid having a viscosity of more than 0.001 Pa s, preferably higher than 0.002 Pa·s, preferably higher than 0.005 Pa·s, preferably higher than 0.01 Pa·s, as measured at 25° C. with apparatus at a shear rate of $100 \text{ s}^{-1}$.

In one embodiment, the liquid vegan food composition is a milk analogue.

In one embodiment, the ratio of total lysine in mg to total protein in g is higher than 30, preferably higher than 40.

In one embodiment, the liquid vegan food composition comprises between 30 wt % and 50 wt % cereal on a dry basis, and between 50 wt % and 70 wt % legume on a dry basis.

In one embodiment, the cereal is oat. In one embodiment, the cereal is quinoa. In one embodiment, the cereal is millet. In one embodiment, the cereal is corn.

In one embodiment, the cereal is biofortified.

In one embodiment, the legume is chickpea. In one embodiment, the legume is lentil.

In one embodiment, the legume is faba bean. In one embodiment, the legume is green pea. In one embodiment, the legume is cowpea.

In one embodiment, the liquid vegan food composition comprises between 13 wt % and 38 wt % protein on a dry basis provided by the cereal and legume.

In one embodiment, the D4,3 particle size of the liquid vegan food composition is less than 100 microns, preferably less than 75 microns, preferably less than 50 microns, preferably less than 40 microns.

In one embodiment, the D4,3 particle size of the liquid vegan food composition is between 20 to 100 microns, or between 30 to 70 microns.

In one embodiment, the D90 particle size of the liquid vegan food composition is less than 300 microns, preferably less than 200 microns, preferably less than 150 microns, preferably less than 100 microns.

In one embodiment, the D50 particle size of the liquid vegan food composition is less than 50 microns, preferably less than 40 microns, preferably less than 30 microns.

Preferably, the particle size is measured using laser diffraction.

The inventors have surprisingly found that a combination of cereal and legume can provide a liquid vegan food composition, which is close to milk and which has the right balance between carbohydrates, fat and protein.

There is also provided a food product comprising the vegan food composition according to the invention.

The invention also provides a method of making a vegan food composition comprising:

a. Mixing at least 5 wt % cereal on a dry basis and at least 10 wt % legume on a dry basis to form a mixture, wherein the D4,3 particle size of the cereal and legume is reduced to less than 200 microns, preferably by milling;

b. Adding an aqueous phase, preferably water;

c. Optionally adding enzyme to prevent gelation, followed by heating, and de-activating the enzyme;

d. Optionally, reducing the D4,3 particle size to below 100 microns, optionally using a colloidal mill and/or homogenization;

e. Reducing particle size so that the D4,3 particle size is less than 65 microns, preferably by micronization or homogenization;

f. Optionally evaporating;

g. sterilizing or pasteurizing; and h. optionally drying.

In one embodiment, the cereal is quinoa. In one embodiment, the cereal is oat. In one embodiment, the cereal is millet. In one embodiment, the cereal is corn.

In one embodiment, the legume is chickpea, preferably roasted chickpea. In one embodiment, the legume is lentil. In one embodiment, the legume is faba bean. In one embodiment, the legume is green pea. In one embodiment, the legume is cowpea.

The enzyme may be alpha amylase;

alpha amylase, beta glucanase and a protease;

an alpha amylase having beta glucanase activity; or an alpha amylase having beta glucanase activity and glucosidase.

In one embodiment, the enzyme is glucosidase.

In one embodiment, the enzyme is added at a concentration of between 0.0001% to 10%.

In one embodiment, micronization is performed to reduce the particle size so that the D4,3 is lower than 100 microns, preferably lower than 75 microns, preferably lower than 50 microns, preferably lower than 40 microns.

In one embodiment, micronization is performed to reduce the particle size so that the D90 is lower than 300 microns, preferably lower than 200 microns, preferably lower than 150 microns, preferably lower than 100 microns, preferably lower than 80 microns.

In one embodiment, micronization is performed to reduce the particle size so that the D50 is lower than 60 microns, preferably lower than 50 microns, preferably between 25 to 50 microns.

Micronization may be performed by Hammer mill, Colloidal mill, Stirred media mill, Bead mill, Jet mill, Ball mill, Pin mill, Roller grinder, Roller refiner, Impact mill, Stone mill, Cryogenic milling, Rod mill, Vibratory mill, or by Cutting mill.

Preferably, micronization is performed using a Hammer mill, Colloidal mill or high pressure homogenization.

High pressure homogenization includes valve homogenization, microfluidization and ultrasonic homogenization.

In one embodiment, no filtration step is used.

In one embodiment, the cereal and legume in step a) are provided as a powder or a flour. A flour is typically ground or milled. A flour is non-fractionated. A flour is not a protein isolate or protein concentrate.

In one embodiment, the cereal and legume in step a) each has a D4,3 particle size of less than 100 microns.

In one embodiment, drying is performed by spray drying, roller drying, belt drying, vacuum belt drying, spray freezing, spray chilling, ray drying, oven drying, convection drying, microwave drying, freeze drying, pulsed electric field assisted drying, ultrasound assisted drying, fluid bed drying, ring drying, vortex drying, or IR drying (radiation).

In a preferred embodiment, drying is performed by spray drying, roller dryer, belt drying, or vacuum belt drying.

In one embodiment, the vegan food composition is deodorized using vacuum at a temperature higher than 40° C.

In an alternative embodiment, method step e) involving micronization is performed before method steps b) and c) involving adding aqueous phase and enzyme.

In one embodiment, the aqueous phase is water.

There is also provided a vegan food composition made by a method according to the invention.

In one embodiment, said composition is a milk analogue.

DETAILED DESCRIPTION

Definitions

When a composition is described herein in terms of wt %, this means a mixture of the ingredients on a dry basis, unless indicated otherwise.

As used herein, "about" is understood to refer to numbers in a range of numerals, for example the range of −30% to +30% of the referenced number, or −20% to +20% of the referenced number, or −10% to +10% of the referenced number, or −5% to +5% of the referenced number, or −1% to +1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 45 to 55 should be construed as supporting a range of from 46 to 54, from 48 to 52, from 49 to 51, from 49.5 to 50.5, and so forth.

As used herein, an "analogue" of a substance is considered to be a parallel of that substance in regard to one or more of its major characteristics. A "milk analogue" as used herein will parallel milk in the major characteristics of purpose, usage, and nutrition. It has similar levels of energy, protein, carbohydrates, vitamins and minerals. Preferably, the milk analogue is an analogue of cow's milk.

The term "vegan food composition" refers to an edible composition which is entirely devoid of animal products, or animal derived products. Non-limiting examples of animal products include meat, eggs, milk, and honey.

The vegan food composition of the invention can be solid, for example a powder or it can be liquid, for example a milk analogue. It can be added to a food product.

Cereal

A cereal is any grass cultivated (grown) for the edible components of its grain (botanically, a type of fruit called a caryopsis), composed of the endosperm, germ, and bran.

The following cereals can be used in the vegan food composition according to the invention: oat, quinoa, maize (corn), rice, wheat, buckwheat, spelt grains, barley, sorghum, millet, rye, triticale, and fonio.

Preferably, the cereal is selected from oat, quinoa, maize (corn), barley, sorghum, millet, rye, triticale, and fonio.

Preferably, the cereal is selected from oat, corn, millet, and quinoa.

Preferably, the cereal is selected from corn, millet, and quinoa.

In one embodiment, the cereal is corn. In one embodiment, the cereal is millet. In one embodiment, the cereal is quinoa.

Legume

A legume is a plant in the family Fabaceae (or Leguminosae), the seed of such a plant (also called pulse). Legumes are grown agriculturally, primarily for human consumption, for livestock forage and silage, and as soil-enhancing green manure.

The following legumes can be used in the vegan food composition according to the invention: lentil, chickpea, beans, and peas, for example kidney beans, navy beans, pinto beans, haricot beans, lima beans, butter beans, azuki beans, mung beans, golden gram, green gram, black gram, urad, fava beans, scarlet runner beans, rice beans, garbanzo beans, cranberry beans, lima beans, green peas, snow peas, snap peas, split peas and black-eyed peas, groundnut, and Bambara groundnut.

Preferably, the legume is selected from lentil, chickpea, beans, mung beans, fava beans, scarlet runner beans, rice beans, green peas, snow peas, snap peas, split peas and black-eyed peas, groundnut, and Bambara groundnut.

Preferably, the legume is selected from lentil, chickpea, cow pea, fava bean (faba bean), and green pea. Preferably, the legume is lentil or chickpea. Preferably, the legume is de-hulled. Preferably, the legume is roasted. Preferably, the legume is de-hulled, roasted chickpea.

Oilseed

In some embodiments, the vegan food composition or food product may further comprises oilseeds, such as sunflower, pumpkin seed, egusi seed, sesame, rapeseed, cotton seed, grapeseed, chia seed, flaxseed, Tamarin seeds, sacha inchi seed, moringa seed, marama seeds, locust bean seeds, melon seeds, watermelon seeds, cucurbit seeds, Okra seeds, Ochro seeds, cacti seeds, cactus seeds, papaya seeds, shea nut, hemp seeds, safflower seeds, and canola seeds.

Preferably, the oilseed is selected from sunflower and sesame.

Dietary Fiber

The preferred range of dietary fiber provided by the legume in the vegan food composition according to the invention is 5 wt % to 25 wt %, more preferably 10 wt % to 20 wt %, most preferably 10 wt % to 15 wt %.

Protein

The preferred range of protein in the vegan food composition according to the invention is 13 wt % to 38 wt %, most preferably 20 wt % to 30 wt %.

Particle Size

All particle sizes described herein apply to reconstituted powder. D4,3, D90 and D50 particle sizes have to be determined by a method adapted to water, for example light scattering.

In one embodiment, the D90 particle size (for the volume weighted size distribution) is less than 300 microns, preferably less than 200 microns, preferably less than 100 microns. D90 (for the volume weighted distribution) is the diameter of particle, for which 90% of the volume of particles have a diameter smaller than this D90.

In one embodiment, micronization is performed to reduce the particle size so that the D50 is lower than 60 microns, preferably lower than 50 microns, preferably lower than 40 microns. D50 (for the volume weighted distribution) is the diameter of particle, for which 50% of the volume of particles have a diameter smaller than this D90. The particle size distribution (weighted in volume) for a powder can be determined by automatized microscopy technique. This may be obtained using a CamSizer (Camsizer XT Retsch) or by dispersing the particle in water using a rotor-stator and performing light scattering. For a liquid, it can be determined using light scattering. In the following text, D90 and D50 are always used for a volume weighted size distribution and describe the particle diameter. Volume weighted size distribution is very familiar for one skilled in the art.

D4,3 particle size distribution in the liquid vegan food composition according to the invention is lower than 100 microns, preferably lower than 75 microns, preferably lower than 50 microns, preferably lower than 40 microns.

Measurement of D4,3 (or D[4,3]) is well known to those skilled in the art as being the sum of the size to the power 4 weighted by their frequency of appearance divided by the sum of the size to the power 3 weighted by their frequency of appearance. The De Brouckere mean diameter is the mean of a particle size distribution weighted by the volume (also called volume-weighted mean diameter, volume moment mean diameter or volume-weighted mean size). It is the mean diameter, which is directly obtained in particle size measurements, where the measured signal is proportional to the volume of the particles. The most prominent examples are laser diffraction and acoustic spectroscopy (Coulter counter).

The De Brouckere mean is defined in terms of the moment-ratio system as, $$D[4, 3] = \frac{\Sigma n_i D_i^4}{\Sigma n_i D_i^3}$$

Where $n_i$ is the frequency of occurrence of particles in size class i, having a mean $D_i$ diameter.

The D90 particle size distribution in the liquid vegan food composition according to the invention is lower than 400 microns, preferably lower than 300 microns, preferably lower than 200 microns, preferably lower than 100 microns, preferably lower than 80 microns.

The D50 particle size distribution in the liquid vegan food composition according to the invention is lower than 50 microns, preferably lower than 40 microns, preferably lower than 30 microns, preferably lower than 20 microns.

Preferably, the particle sizes of liquid compositions are measured using laser diffraction.

Preferably, the particle sizes of powders are measured using image analysis.

Fat

The preferred range of fat content of the liquid vegan food composition according to the invention is between 0-35 wt %, preferably 1-35 wt %, preferably between 3-30 wt %, preferably between 5-15 wt %.

Carbohydrate

The preferred range of carbohydrate content of the liquid vegan food composition according to the invention is 25 wt % to 50 wt %, which does not include contribution from the dietary fibers of the composition.

Protein Quality

Protein quality is closely associated with the various essential amino acid ratios. The amino acid ratio for a given essential amino acid is defined by the quantity of this essential amino acid in mg divided by total protein in g. There are accepted standard values for these ratios for each essential amino acid (Protein quality evaluation, Report of the joint FAO-WHO Expert Consulation Bethesda Md. USA 4-8 Dec. 1989), which defines if a protein source contains enough of this essential amino acid. For many protein sources such as nuts, seeds and cereals, the limiting amino acid is lysine and in addition, lysine degrades during food processing due to association with other nutrients and Maillard reaction (Tomé, D. & Bos, C. Lysine requirement through the human life cycle. *Journal of Nutrition* 137, 1642S-1645S (2007)). It should be noted that in a final product, lysine amount is even lower due to chemical reaction. The amino acid ratio for a given essential amino acid is defined by the quantity of this essential amino acid in mg divided by total protein in g. The normalized amino acid ratio for any essential amino acids refers to the amino acid ratio divided by a standard essential amino acid quantity for each amino acid. This standard amino acid quantity is taken for lysine to be 48 mg/g of protein, for theorine 25 mg/g, for Isoleucine 30 mg/g, for leucine 61 mg/g, for valine 40 mg/g, for histidine 16 mg/g, and aromatic amino acids, which are the sum phenylalamine+tyrosine, 41 mg/g. Sulphurous amino acids, which are the sum methyonine and cysteine, 23 mg/g and triptophan 6.6 mg/g. These values are in accordance with recommendations for kids older than 4 years, adolescents and adults (FAO. Dietary protein quality evaluation in human nutrition. Report of an FAO Expert Consultation. FAO Food and Nutrition Paper 92. 2013). The amino acid score is the lowest value of all the normalized amino acid ratio corresponding to there amino acids cited above. The amino acid score should be higher than 0.7, preferably higher than 0.8, preferably higher than 0.85, preferably higher than 0.9, preferably higher than 0.95.

Vegan Food Composition

In one embodiment, the cereal is quinoa and the legume is lentil. In one embodiment, the cereal is oat and the legume is chickpea.

In one embodiment, the vegan food composition is a milk analogue comprising 40 to 60 wt %, preferably about 50 wt % quinoa and 40 to 60 wt %, preferably 50 wt % lentil on a dry basis, wherein said composition comprises between 5 to 15 wt %, preferably about 9.4 wt % dietary fiber and between 10 to 20 wt %, preferably about 15 wt % protein, and wherein the D4,3 is less than 100 microns, preferably between 40 to 80 microns.

In one embodiment, the vegan food composition is a powder comprising 25 to 45 wt %, preferably about 35 wt % oat and 55 to 75 wt %, preferably about 65 wt % chickpea on a dry basis, wherein said composition comprises between 5 to 20 wt % preferably about 13 wt % dietary fiber and between 1 to 10 wt %, preferably about 6.5 wt % protein, and wherein the D4,3 is less than 50 microns, preferably between 20 to 50 microns.

Food Product

In one embodiment, there is provided a food product comprising the vegan food composition according to the invention. The food product can be, for example, a vegan milk analogue based product, Nesquik, Milo, apple puree and other fruit extracts, strawberry puree, creams, culinary sauces, chocolate and other confectionary.

In one embodiment, the food product can be a vegan cream analogue.

In one embodiment, the food product has a viscosity of less than 5 Pa s, preferably of less than 0.8 Pa s, preferably of less than 0.5 Pa s, preferably of less than 0.1 Pa s, preferably of less than 0.05 Pa s, as measured at 25° C. with apparatus at a shear rate of 100 s$^{-1}$.

In one embodiment, the food product has a viscosity of less than 5.5 Pa s, preferably of less than 0.9 Pa s, preferably of less than 0.55 Pa s, preferably of less than 0.11 Pa s, preferably of less than 0.055 Pa s, as measured at 25° C. with apparatus at a shear rate of 100 s$^{-1}$.

In one embodiment, the vegan food composition is a liquid having a viscosity of more than 0.001 Pa s, preferably higher than 0.002 Pa·s, preferably higher than 0.005 Pa·s, preferably higher than 0.01 Pa·s, as measured at 25° C. with apparatus at a shear rate of 100 s$^{-1}$.

Process

In one embodiment, the invention relates to a method of making a vegan food composition comprising mixing cereal and legume. The cereal is preferably quinoa or oat. The legume is preferably chickpea or lentil.

The chickpea are preferably roasted.

For the pre-grinding step, 50 wt % quinoa can be dry mixed with 50 wt % lentil. The size is then reduced, preferably by milling, preferably to a D90 less than 1000 microns.

For the enzymatic treatment step, the mixture is preferably diluted in water (10 to 20% TS (total solids)). Pre-gelatinization can then be performed at about 90° C. for about 15 mins. Alpha amylase can then be added for 15 mins at 80° C., followed by a deactivation step, for example at 121° C. for at least 3 min.

For the micronization step, the mixture can be subjected to ball milling, homogenization, for example valve homogenization, to get a D90 lower than 400 microns, preferably lower than 300 microns, preferably lower than 200 microns, more preferably lower than 100 microns, most preferably lower than 80 microns.

The homogenization step may be carried out, for example, at a pressure of 250 bar and then at 50 bar.

In one embodiment, the invention relates to a method of making a vegan composition comprising mixing oat and chickpea. In one embodiment, the invention relates to a method of making a vegan composition comprising mixing lentil and quinoa.

For the pre-grinding step, 50 wt % cereal is dry mixed with 50 wt % legume. The D90 particle size is then reduced, preferably by hammer milling, preferably to a D90 particle size of less than 1000 microns.

Pre-gelatinization can then be performed at about 90° C. for about 15 mins. Alpha amylase can then be added for 80° C. for at least 15 mins, followed by a deactivation step, for example at 135° C. for at least 10 s.

Two passages of ball milling may then be applied, for example at 500 rpm for at least 10 min.

In one embodiment, the method comprises:

a. Mixing at least 5 wt % cereal on a dry basis and at least 10 wt % legume on a dry basis to form a mixture, wherein D4,3 particle size of the cereal and legume is reduced to less than 200 microns, preferably by milling;

b. Adding an aqueous phase, preferably water;

c. Adding enzyme to prevent gelation, followed by heating, and de-activating the enzyme;

d. Reducing the D4,3 particle size to below 100 microns, optionally using a colloidal mill and/or homogenization;

e. Reducing particle size so that the D4,3 particle size is less than 65 microns, preferably by micronization or homogenization;

f. Optionally evaporating;

g. Sterilizing or pasteurizing; and h. Optionally drying.

In one embodiment, the method comprises:

a. Mixing at least 5 wt % cereal on a dry basis and at least 10 wt % legume on a dry basis to form a mixture, wherein D4,3 particle size of the cereal and legume is reduced to less than 200 microns, preferably by milling;

b. Adding an aqueous phase, preferably water;

c. Adding enzyme to prevent gelation, followed by heating, and de-activating the enzyme;

d. Reducing the D4,3 particle size to below 100 microns, optionally using a colloidal mill and/or homogenization;

e. Reducing particle size so that the D4,3 particle size is less than 65 microns, preferably by micronization or homogenization;

f. Evaporating;

g. Sterilizing or pasteurizing; and h. Drying.

In one embodiment, the method comprises:

a. Mixing at least 5 wt % cereal on a dry basis and at least 10 wt % legume on a dry basis to form a mixture, wherein D4,3 particle size of the cereal and legume is reduced to less than 200 microns by milling;

b. Adding an aqueous phase, preferably water;

c. Adding enzyme to prevent gelation, followed by heating, and de-activating the enzyme;

d. Reducing the D4,3 particle size to below 100 microns using a colloidal mill and/or homogenization;

e. Reducing particle size so that the D4,3 particle size is less than 65 microns by micronization or homogenization;

f. Evaporating;

g. Sterilizing or pasteurizing; and h. Drying.

EXAMPLES

Example 1: Beverage Comprising Chickpea and Oat

Chickpeas were supplied by Zwickie (Switzerland). Chickpea de-hulling was carried out using Laboratory shelling Machine (F.H. SCHULE Mühlenbau GmbH, Germany) for 90 s and at 90% of maximum speed.

The chickpeas were then roasted using a Salvis combisteam CSC furnace (Germany) operating at 160° C. for 40 minutes. 65% Chickpea grains were mixed with 35% oat seeds (Demeter). The size of the particles was reduced by Hammer milling operating at speed 2 with 12 knifes and grid size 0.5 mm (Retsch ZM1, Switzerland). 30% of this mixture was mixed with 70% water. To further reduce the grain size, the mixture was passed in a colloid mill (Ika Labor Pilot) having a gap of 50 microns. The dispersion was then diluted in water to have 12% of solid matter. The mixture was heated under agitation for 15 minutes at 90° C., followed by cooling down to 80° C. 0.0025 wt %, in reference to total dispersion weight, of Ban 800 (Novozymes, Denmark) was added, where the main active component is the enzyme alpha amylase. The temperature was maintained at 80° C. and agitation was carried out for 15 minutes. The dispersion was then heated at 122° C. for 3 minutes to deactivate the enzymes. The liquid was diluted to a total solid of 9% and passed two times through a Niro Panda Plus homogenizer using pressure of 250/50 bars. A nice ready to drink was obtained. The protein composition was determined by the Dumas method with a conversion factor of 6.25. The lipid composition was determined by acid hydrolysis. The composition of nutrients in weight % on a dry basis was as follows: protein: 15%, Fat: 6.5%, Fibre: 13% and carbohydrate (except fiber): 60%. The particle size was determined using a Malvern 3000 instrument using the Mie model with stirrer speed 2000, material name: protein, refractive index 1.54, particle density 1.2 and absorption index 0.01, dispersant was water and corresponding refractive index 1.33. Result is the average of 5 measurements. D4,3 was 34 microns, Dx(90) was found to be 82 microns while the Dx(50) was 20 microns. The drink has a pleasant taste and a smooth texture.

Example 2: Beverage Comprising Lentil and Quinoa

50% yellow lentils (Bio Coop Naturaplan) were mixed with 50% Quinoa seeds. 30% of this mixture was mixed with 70% water and let soak overnight at 4° C. The mixture was first passed through a Bamix blinder. To finely mill the grain and the seeds, the mixture was then passed in a colloid mill (Ika Labor Pilot) having a gap of 50 microns. The dispersion was then diluted in water to have 12% of solid matter. The mixture was heated under agitation for 15 minutes at 90° C., followed by cooling down to 80° C. 0.0025 wt %, in reference to total dispersion weight, of Ban 800 (Novozymes, Denmark) was added, where the main active component is the enzyme alpha amylase. The temperature was maintained at 80° C. and agitation was carried out for 15 minutes. The dispersion was then heated at 122° C. for 3 minutes to deactivate the enzymes. The dispersion was pre-homogenized using a rotor stator device IKA PT3100 1 min at 15000 rpm. The liquid was passed two times through a Niro Panda Plus homogenizer using pressure of 250/50 bars. A nice ready to drink was obtained. The composition of nutrients in weight % on a dry basis was as follows: protein: 22%, Fat: 4.5%, Fibre: 9.4% and carbohydrate (excluding fiber): 59%. The particle size was determined using a Malvern 3000 instrument using the Mie model with stirrer speed 2000, material name: protein, refractive index 1.54, particle density 1.2 and absorption index 0.01, dispersant was water and corresponding refractive index 1.33. Result is the average of 5 measurements. D4,3 was found to be 63 microns, Dx(90) was found to be 134 microns while the Dx(50) was 43 microns. The drink has a pleasant taste and a smooth texture.

Example 3: Beverage Comprising Fava Bean, Almond, and Corn

40% Fava bean was mixed with 35% almond flour (AOT, Germany) and 25% corn flour (polenta). The size of the particles was reduced by Hammer milling operating at speed 2 with 12 knifes and grid size 0.5 mm (Retsch ZM1, Switzerland). 490 g of deionized water was added to 210 g of the milled mixture. The suspension was then passed 2 times in a colloid mill (Ika Labor Pilot) having a gap of 50 microns. The mixture was then diluted to a total solid of 15%. It was heated under agitation for 15 minutes at 90° C., followed by cooling down to 80° C. 0.0025 wt %, in reference to total dispersion weight, of Ban 800 (Novozymes, Denmark) was added, where the main active component is mainly the enzyme alpha amylase. The temperature was maintained at 80° C. and agitation was carried out for 15 minutes. The dispersion was then heated at 122° C. for 3 minutes to deactivate the enzymes. The liquid was passed three times through a Niro Panda Plus homogenizer using pressure of 350/50 bars. The nutrient composition in weight % on a dry basis was as follows: Protein was 30%, fat: 6%, Fiber 17% and carbohydrate 33%. The particle size was determined using a Malvern 3000 instrument using the Mie model with stirrer speed 2000, material name: protein, refractive index 1.54, particle density 1.2 and absorption index 0.01, dispersant was water and corresponding refractive index 1.33. Result is the average of 5 measurements. D4,3 was found to be 32 microns, Dx(90) was found to be 65 microns while the Dx(50) was 25 microns.

Example 4: Beverage Comprising Chickpea, Oat, and Sunflower Oil

Chickpeas were supplied by Zwickie (Switzerland). Chickpea de-hulling was carried out using Laboratory shelling Machine (F.H. SCHULE Mühlenbau GmbH, Germany) for 90 s and at 90% of maximum speed. The chickpeas were then roasted using a Salvis combisteam CSC furnace (Germany) operating at 160° C. for 40 minutes. 65% Chickpea grains were mixed with 35% oat seeds (Demeter). The size of the particles was reduced by Hammer milling operating at speed 2 with 12 knifes and grid size 0.5 mm (Retsch ZM1, Switzerland). 30% of this mixture was mixed with 70% water. To further reduce the grain size, the mixture was passed in a colloid mill (Ika Labor Pilot) having a gap of 50 microns. The dispersion was then diluted in water to have 12% of solid matter. The mixture was heated under agitation for 15 minutes at 90° C., followed by cooling down to 80° C. 0.0025 wt %, in reference to total dispersion weight, of Ban 800 (Novozymes, Denmark) was added, where the main active component is the enzyme alpha amylase. The temperature was maintained at 80° C. and agitation was carried out for 15 minutes. The dispersion was then heated at 122° C. for 3 minutes to deactivate the enzymes. The liquid was diluted to Ts 8% and 8 g of high oleic sunflower oil was added to 92 g of water. The mixture was prehomogenized using a rotor/stator device. It was then passed two times through a Niro Panda Plus homogenizer using pressure of 250/50 bars. The composition of nutrients in weight % on a dry basis was as follows: protein: 8%, Fat: 52%, Fibre: 6% and carbohydrate (except fiber): 29%. The particle size was determined using a Malvern 3000 instrument using the Mie model with stirrer speed 2000, material name: protein, refractive index 1.54, particle density 1.2 and absorption index 0.01, dispersant was water and corresponding refractive index 1.33. Result is the average of 5 measurements. D4,3 was 31 microns, Dx(90) was found to be 79 microns while the Dx(50) was 19 microns. The drink has a pleasant taste and a smooth and creamy texture.

Example 5: Beverage Comprising Chickpea, Sunflower, and Oat Obtained by Colloid Mill at Kitchen Scale Chickpeas were sourced from Vivien Paille (France). Chickpea de-hulling was carried out using Laboratory shelling Machine (F.H. SCHULE Mühlenbau GmbH, Germany) for 90 s and at 90% of maximum speed. The chickpeas were then roasted using a Salvid combisteam CSC furnace (Germany) operating at 160° C. for 40 minutes. 45% chickpea was mixed with 20% oat grains. A chickpea/oat powder was obtained using hammer milling (Retsch ZM1, Switzerland) operating at speed 2 with 12 knifes and grid size of 0.5 mm. 65 wt % of the obtained chickpea/oat powder was dry mixed with 35 wt % (partially) defatted sunflower flour (Heliaflor 45, Austrade, Germany). 30% of the obtained mixture was mixed with 70% of water. To refine the size, the obtained dispersion was passed in a colloidal mill (Ika Labor Pilot)

having a gap of 50 microns. The dispersion was then diluted in water to have 12% of solid matter. The mixture was heated under agitation for 15 minutes at 90° C., followed by cooling down to 80° C. 0.0025 wt %, in reference to total dispersion weight, of Ban 800 (Novozymes, Denmark) was, added, where the main active component is the enzyme alpha amylase. The temperature was maintained at 80° C. and agitation was carried out for 15 minutes. The dispersion was then heated at 121° C. for 3 minutes to deactivate the enzymes. It was then diluted to 8.5% solid. The liquid was passed through a Nyro Panda Plus homogenizer with pressure 300/50 bars. The particle size was determined using a Malvern 3000 instrument using the Mie model with stirrer speed 2000, material name: protein, refractive index 1.54, particle density 1.2 and absorption index 0.01, dispersant was water and corresponding refractive index 1.33. Result is the average of 5 measurements. The D4,3 was found to be 38 microns, the D90 was found to be 82 microns and the D50 22 microns. The tasted product was very smooth with no graininess and has a pleasant nutty taste. The composition of nutrients in weight % on a dry basis was as follows: protein: 28%, Fat: 8.5%, Fibre: 13% and carbohydrate (except fiber): 46%.

Example 6: Beverage Comprising Chickpea, Sunflower and Oat Obtained at Pilot Plant Scale, Colloidal Mill Before Enzymatic Treatment Chickpeas were sourced from Vivien Paille (France). Chickpea de-hulling was carried out using Laboratory shelling Machine (F.H. SCHULE Mühlenbau GmbH, Germany) for 90 s and at 90% of maximum speed. The chickpeas were then roasted using a Salvid combisteam CSC furnace (Germany) operating at 160° C. for 40 minutes. 45% chickpea was mixed with 20% oat grains. A chickpea/oat powder was obtained using hammer milling (Retsch ZM1, Switzerland) operating at speed 2 with 12 knifes and grid size of 0.5 mm. 65 wt % of the obtained chickpea/oat powder was dry mixed with 35 wt % (partially) defatted sunflower flour (Heliaflor 45, Austrade, Germany). 30% of the obtained mixture was mixed with 70% of water. 30% of the chickpea/sunflower/oat flour was introduced into water and the dispersion was mixed using a Mitec RG 1-51. To refine the size, the obtained dispersion was passed in a colloidal mill (Process pilot 2000-4 IKA-Werke in Coloidal milling configuration) having a gap of 50 microns. The dispersion was then diluted in water to have 12% of solid matter. The dispersion was then introduced into a Tetra Almix B200-100 VA Scanima reactor (Germany). The mixture was heated under agitation for 15 minutes at 90° C., followed by cooling down to 80° C. 0.003 wt %, in reference to the total dispersion mass, of Ban 800 (Novozymes, Denmark), where the main active component is the enzyme alpha amylase was added. The temperature was maintained at 80° C. and agitation was carried out for 15 minutes. The mixture was then heated for 81 seconds in an APV HTST (Germany) at 135° C. to deactivate the alpha amylase. A filtration was operated using a 0.3 mm sieve (Retsch). Homogenization (APV, HTST, Germany) was realized using pressure of 350/50 Bars. During all the operations in liquid, the pH was adjusted either with NaOH or with HCl to maintain pH between 6.3 and 6.8. 0.02 g/100 g of protein masker flavor (article number 513540 TP1704, Firmenich) and 0.03 g/100 g of vanilla flavour (article number NE819643, IFF) were added into the liquid. The dispersion was treated by ultra high temperature treatment using a temperature of 139° C. for 5 seconds (APV, HTST, Germany). The particle size was determined using a Malvern 3000 instrument using the Mie model with stirrer speed 2000, material name: protein, refractive index 1.54, particle density 1.2 and absorption index 0.01, dispersant was water and corresponding refractive index 1.33. Result is the average of 5 measurements. The D4,3 was found to be 35 microns, the D90 was found to be 92 microns and the D50 15 microns. No significant difference in particle size was observed due to the aroma addition. A delicious drink with mouthfeel and nutty taste was obtained.

The composition of nutrients in weight % on a dry basis was as follows: protein 29%, fat 12%, Dietary fiber 13% and carbohydrate 41%. Viscosity was measured using a Physica MCR 501 (Anton Paar), with a Pelletier temperature of 25° C., with 15 points for 20 seconds. Bob length was 40 mm, bob diameter was 26.65 mm, cup diameter was 28.92 mm and active length: 120.2 mm. Viscosity was 0,035 Pas measured at a shear rate of 100 s$^{-1}$.

Example 7: Beverage Comprising Chickpea, Sunflower, and Oat Obtained at Pilot Plant Scale, Colloidal Mill after Enzymatic Treatment Chickpeas were sourced from Vivien Paille (France). Chickpea de-hulling was carried out using Laboratory shelling Machine (F.H. SCHULE Mühlenbau GmbH, Germany) for 90 s and at 90% of maximum speed. The chickpeas were then roasted using a Salvid combisteam CSC furnace (Germany) operating at 160° C. for 40 minutes. 45% chickpea was mixed with 20% oat grains. A chickpea/oat powder was obtained using hammer milling (Retsch ZM1, Switzerland) operating at speed 2 with 12 knifes and grid size of 0.5 mm. 65 wt % of the obtained chickpea/oat powder was dry mixed with 35 wt % (partially) defatted sunflower flour (Heliaflor 45, Austrade, Germany). 15% of the chickpea/sunflower/oat flour, was introduced into water and the dispersion was mixed using a Mitec RG 1-51. The dispersion was then introduced into a Tetra Almix B200-100 VA Scanima reactor (Germany). The mixture was heated under agitation for 15 minutes at 90° C., followed by cooling down to 80° C. 0.0025 wt %, in reference to the total dispersion mass, of Ban 800 (Novozymes, Denmark), where the main active component is the enzyme alpha amylase, was added. The temperature was maintained at 80° C. and agitation was carried out for 15 minutes. To refine the size, the obtained dispersion was passed in a colloid mill (Process pilot 2000-4 IKA-Werke in Colloid milling configuration) having a gap of 50 microns. The dispersion was then diluted in water to have 12% of solid matter. Homogenization (APV, HTST, Germany) was realized using pressure of 300/50 Bars. During all the operations in liquid, the pH was adjusted either with NaOH or with HCl to maintain pH between 6.3 and 6.8. The liquid was then diluted with water so that a TS of 9% is obtained. The liquid was treated by ultra-high temperature treatment (UHT) using a temperature of 139° C. for 5 seconds (APV, HTST, Germany).

The D4,3 was found to be 35 microns, the D90 was found to be 92 microns and the D50 15 microns. No significant difference in particle size was observed due to the aroma addition. A delicious drink with mouthfeel and nutty taste was obtained.

The composition of nutrients in weight % on a dry basis was as follows: protein 28.5%, fat 8.6%%, Dietary fiber 11% and carbohydrate 47%. The measured amino acids for 100 g dispersion was for Lysine, L: 0,117 g; Phenylalanine, L: 0.13 g; Histidine L: 0,064 g, Isoleucine: 0,106 g, Leucine L: 0,172 g, threonine, L: 0,097 g, Tyrosine, L: 0,073 g, valine, L: 0,124 g, cysteine: 0.04 g, methionine L: 0,051 g, tryptophan L: 0,034 g. Taking into consideration that protein content is 2.62%, an amino score of 0.93 is obtained, lysine being the limiting amino acid.

Example 8: Beverage Comprising Chickpea, Sunflower, and Oat Obtained by Ball Milling at Kitchen Scale Chickpeas were sourced from Vivien Paille (France). Chickpea de-hulling was carried out using Laboratory shelling Machine (F.H. SCHULE Mühlenbau GmbH, Germany) for 90 s and at 90% of maximum speed. The chickpeas were then roasted using a Salvid combisteam CSC furnace (Germany) operating at 160° C. for 40 minutes. 45% of chickpea was mixed with 20% of oat and a chickpea/oat flour was obtained using hammer milling (Retsch ZM1, Switzerland) operating at speed 2 with 12 knifes and grid size of 0.5 mm. 65 wt % of the obtained chickpea/oat flour was dry mixed with 35 wt % of (partially) defatted sunflower flour (Heliaflor 45, Austrade, Germany). 12% of the chickpea/sunflower/oat flour, was introduced and mixed into water. The dispersion was then introduced into a Tetra Almix B200-100 VA Scanima reactor (Germany). The mixture was heated under agitation for 15 minutes at 90° C., followed by cooling down to 80° C. 0.003 wt %, in reference to the total dispersion mass, of Ban 800 (Novozymes, Denmark), where the main active component is the enzyme alpha amylase was added. The temperature was maintained at 80° C. and agitation was carried out for 15 minutes. The mixture was then heated for 81 seconds in an APV HTST (Germany) at 135° C. to deactivate the alpha amylase. Two passages of Ball-milling (Retsch PM200, Germany) were then applied at 500 rpm, 10 min. The Dx(90) was found to be 93 microns and the Dx(50) 22 microns with a D(4; 3) of 45 microns.

Example 9: Beverage Comprising Cowpea, Hemp and Millet

40% cowpea was mixed with 40% hemp seeds and 20% millet grains. The size of the particles was reduced by Hammer milling operating at speed 2 with 12 knifes and grid size 0.75 mm (Retsch ZM1, Switzerland). 490 g of deionized water was added to 210 g of the milled mixture. The suspension was then passed 2 times in a colloid mill (Ika Labor Pilot) having a gap of 50 microns. The mixture was then diluted to a total solid of 15%. It was heated under agitation for 15 minutes at 90° C., followed by cooling down to 80° C. 0.0025 wt %, in reference to total dispersion weight, of Ban 800 (Novozymes, Denmark) was added, where the main active component is mainly the enzyme alpha amylase. The temperature was maintained at 80° C. and agitation was carried out for 15 minutes. The dispersion was then heated at 122° C. for 3 minutes to deactivate the enzymes. The dispersion was diluted to a total solid of 10%. The liquid was passed three times through a Niro Panda Plus homogenizer using pressure of 350/50 bars.

The nutrient composition in weight % on a dry basis was as follows: Protein 24%, fat: 21%, Fiber 7% and carbohydrate 34%. The particle size was determined using a Malvern 3000 instrument using the Mie model with stirrer speed 2000, material name: protein, refractive index 1.54, particle density 1.2 and absorption index 0.01, dispersant was water and corresponding refractive index 1.33. Result is the average of 5 measurements. D4,3 was found to be 24 microns, Dx(90) was found to be 47 microns while the Dx(50) was 21 microns.

Example 10: Beverage Comprising Chickpea, Sunflower/Oat, and Olive Oil

Chickpeas were sourced from Vivien Paille (France). Chickpea de-hulling was carried out using Laboratory shelling Machine (F.H. SCHULE Mühlenbau GmbH, Germany) for 90 s and at 90% of maximum speed. The chickpeas were then roasted using a Salvid combisteam CSC furnace (Germany) operating at 160° C. for 40 minutes. 45% chickpea was mixed with 20% oat grains. A chickpea/oat powder was obtained using hammer milling (Retsch ZM1, Switzerland) operating at speed 2 with 12 knifes and grid size of 0.5 mm. 65 wt % of the obtained chickpea/oat powder was dry mixed with 35 wt % (partially) defatted sunflower flour (Heliaflor 45, Austrade, Germany). 30% of the obtained mixture was mixed with 70% of water. To refine the size, the obtained dispersion was passed in a colloidal mill (Ika Labor Pilot) having a gap of 50 microns. The dispersion was then diluted in water to have 12% of solid matter. The mixture was heated under agitation for 15 minutes at 90° C., followed by cooling down to 80° C. 0.0025 wt %, in reference to total dispersion weight, of Ban 800 (Novozymes, Denmark) was added, where the main active component is the enzyme alpha amylase. The temperature was maintained at 80° C. and agitation was carried out for 15 minutes. The dispersion was then heated at 121° C. for 3 minutes to deactivate the enzymes. It was then diluted to 8.5% solid. 7 g olive oil was added for 93 g of the dispersion and was pre-homogenized using a rotor stator. The liquid was passed through a Nyro Panda Plus homogenizer with pressure 300/50 bars. The particle size was determined using a Malvern 3000 instrument using the Mie model with stirrer speed 2000, material name: protein, refractive index 1.54, particle density 1.2 and absorption index 0.01, dispersant was water and corresponding refractive index 1.33. Result is the average of 5 measurements. The D4,3 was found to be 35 microns, the D90 was found to be 81 microns and the D50 20 microns. The tasted product was very smooth and creamy with no graininess and has a pleasant nutty taste. The composition of nutrients in weight % on a dry basis was as follows: protein 15%, fat 47.5%, Dietary fiber 7% and carbohydrate 25.0%.

Example 11: Beverage Comprising Chickpea/Sunflower/Oat Powder with Amylase Treatment Obtained at Pilot Plant Scale Chickpeas were sourced from Vivien Paille (France). Chickpea de-hulling was carried out using shelling Machine (F.H. SCHULE Mühlenbau GmbH, Germany) for 100 s and at 90% of maximum speed. The chickpeas were then roasted using a Salvid combisteam CSC furnace (Germany) operating at 160° C. for 40 minutes. 45% chickpea was mixed with 35 wt % (partially) defatted sunflower flour (Heliaflor 45, Austrade, Germany) and 20% oat grains. The premix was treated in a hammer milling (Retsch ZM1, Switzerland) operating at speed 2 with 12 knifes and grid size of 0.5 mm in order to produce a homogeneous premix. 12% of the obtained mixture was mixed with 88% of water. The dispersion was then introduced into a Tetra Almix B200-100 VA Scanima reactor (Germany). The mixture was heated under agitation for 15 minutes at 90° C., followed by cooling down to 80° C. 0.003 wt %, in reference to the total dispersion mass, of Ban 800 (Novozymes, Denmark) which contains the enzyme alpha amylase as active component was added. The temperature was kept at 80° C. and agitation was carried out for 15 minutes. For further refining, the obtained dispersion was passed through a colloidal mill (Process pilot 2000-4 IKA-Werke in Colloidal milling configuration) having a gap of 50 microns and two homogenization steps (APV, HTST, Germany) using pressure of 300/50 Bars. For enzyme inactivation the dispersion was treated by ultra high temperature using a temperature of 143° C. for 5 seconds (APV, HTST, Germany). The liquid was concentrated to reach a target viscosity of 100 mPa s (60° C. and 600 l/s). In order to obtain a powder the dispersion was dried using a Niro spray dryer (model SD-6.3N, GEA). The liquid was atomized by means of a bifluid nozzle and the inlet air temperature entered the drying chamber at 140° C.

Viscosity of the Preparation at 25% TS

The viscosity was measured in a modular compact rheometer (Anton PAAR, Graz) with a concentrical cylinder system at a temperature of 60° C.

100 l/s: 1138.3±1.7 maP*s
    600 l/s: 342.6±0.4 mPa*s
    TS limit for spray drying at 60° C.: 20.4%

Particle Size:

Wet method: Particle size in water was measured with a Mastersizer 2000 (Malvern instruments Ltd., United Kingdom), using laser diffraction. Samples were dispersed in a Hydro 2000 G water dispersion unit (Malvern instruments Ltd., United Kingdom) at room temperature. Characteristic particle size $d_{10}$, $d_{50}$ and $d_{90}$ are calculated from normalized curves, corresponding to the particle size of 10%, 50% and 90% of the particles respectively.

Dry method: Particle size of powders was measured by Camsizer XT (Retsch Technology GmbH, Germany). The technique of digital image analysis is based on the computer processing of a large number of sample's pictures taken at a frame rate of 277 images/seconds by two different cameras, simultaneously. Characteristic particle size $d_{10}$, $d_{50}$ and $d_{90}$ are calculated from normalized curves, corresponding to the particle size of 10%, 50% and 90% of the particles respectively.

| Particle size | D10 [μm] | D50 [μm] | D90 [μm] | D4,3 [μm] |
|---|---|---|---|---|
| Wet; before drying | 3.2 | 27.5 | 103 | 53.3 |
| Dry, Powder | 9.9 | 30.4 | 120.2 | 65.6 |

Example 12: Beverage Comprising Chickpea/Sunflower/Oat Powder with Amylase, Beta-Glucanase & Protease Obtained at Pilot Plant Scale Chickpea flour (69%) and oat flour (31%) were mixed into water (40° C.) at a total solids content of 7.8%. The dispersion was then introduced into a Tetra Almix B200-100 VA Scanima reactor (Germany) and heated to 60° C. The starch degrading enzyme alpha-amylase (Termamyl Classic, Novozymes, Denmark) was added at a quantity of 0.006 wt. %, in reference to total dispersion mass (including sunflower). The mixture was heated under agitation to 90° C. and kept at this temperature for 4 minutes, followed by cooling down to 56° C. At 56° C. defatted sunflower flour (35%) and the enzyme beta-glucanase (Viscozyme L, Novozymes, Denmark) for beta-glucan degradation at a quantity of 0.002 wt. %, in reference to total dispersion mass, was added and the incubation time was 20 minutes. Afterwards, the protein hydrolysing enzyme protease (PRO-TIN SD-NY10, Amano, Japan) was added at a concentration of 0.005 wt. %, in reference to total dispersion mass, and the incubation time was another 20 minutes. For enzyme inactivation the dispersion was treated by ultra-high temperature using a temperature of 143° C. for 5 seconds (APV, HTST, Germany). After enzyme inactivation, defatted sunflower flour (35%) was added to the chickpea/oat mix (65%) leading to a total solids content of 12%. For further refining, the obtained dispersion was passed through a colloidal mill (Process pilot 2000-4 IKA-Werke in Colloidal milling configuration) having a gap of 50 microns and two homogenization passes (APV, HTST, Germany) using pressure of 300/50 Bars. The liquid was concentrated to reach a target viscosity of 100 mPa s (60° C. and 600 l/s). The concentrate was dried using a Niro spray dryer (model SD-6.3N, GEA). The liquid was atomized by means of a bifluid nozzle and the inlet air temperature entered the drying chamber at 140° C. The enzymatic treatments and addition of sunflower after UHT treatment were strategies to decrease the viscosity in order to allow a more efficient spray drying process.

Viscosity of the Preparation at 25% TS

Method: The viscosity was measured in a modular compact rheometer (Anton PAAR, Graz) with a concentrical cylinder system at a temperature of 60° C.

Results:

100 l/s: 436.1±13.1

600 l/s: 137.6±1.8

TS limit for spray drying at 60° C.: 23.6%

Particle Size:

Wet method: Particle size in water was measured with a Mastersizer 2000 (Malvern instruments Ltd., United Kingdom), using laser diffraction. Samples were dispersed in a Hydro 2000 G water dispersion unit (Malvern instruments Ltd., United Kingdom) at room. Characteristic particle size $d_{10}$, $d_{50}$ and $d_{90}$ are calculated from normalized curves, corresponding to the particle size of 10%, 50% and 90% of the particles respectively.

Dry Method:

Particle size of powders was measured by Camsizer XT (Retsch Technology GmbH, Germany). The technique of digital image analysis is based on the computer processing of a large number of sample's pictures taken at a frame rate of 277 images/seconds by two different cameras, simultaneously. Characteristic particle size $d_{10}$, $d_{50}$ and $d_{90}$ are calculated from normalized curves, corresponding to the particle size of 10%, 50% and 90% of the particles respectively.

| Particle size | D10 [µm] | D50 [µm] | D90 [µm] | D4,3 [µm] |
|---|---|---|---|---|
| Wet; before drying | 2.0 | 35.5 | 125 | 96.4 |
| Dry, Powder | 10.1 | 31.3 | 185.9 | 88.4 |

Example 13: Beverage Comprising Chickpea/Sunflower/Oat Powder with Amylase, Beta-Glucanase & Protease; Low Heat Impact on Sunflower Obtained at Pilot Plant Scale Chickpea flour (69%) and oat flour (31%) were mixed into water (40° C.) at a total solids content of 7.8%. The dispersion was then introduced into a Tetra Almix B200-100 VA Scanima reactor (Germany) and heated to 60° C. The starch degrading enzyme alpha-amylase (Termamyl Classic, Novozymes, Denmark) was added at a quantity of 0.006 wt. %, in reference to total dispersion mass (including sunflower). The mixture was heated under agitation to 90° C.

and kept at this temperature for 4 minutes, followed by cooling down to 56° C. At 56° C. the enzyme beta-glucanase Viscozyme L, Novozymes, Denmark) for beta-glucan degradation at a quantity of 0.002 wt. %, in reference to total dispersion mass (including sunflower), was added and the incubation time was 20 minutes. Afterwards, the protein hydrolysing enzyme protease (PROTIN SD-NY10, Amano, Japan) was added at a concentration of 0.005 wt. %, in reference to total dispersion mass (including sunflower), and the incubation time was another 20 minutes. For enzyme inactivation the dispersion was treated by ultra high temperature using a temperature of 143° C. for 5 seconds (APV, HTST, Germany). After enzyme inactivation, defatted sunflower flour (35%) was added to the chickpea/oat mix (65%) leading to a total solids content of 12%. For further refining, the obtained dispersion was passed through a colloidal mill (Process pilot 2000-4 IKA-Werke in Colloidal milling configuration) having a gap of 50 microns and two homogenization passes (APV, HTST, Germany) using pressure of 300/50 Bars. The liquid was concentrated to reach a target viscosity of 100 mPa s (60° C. and 600 l/s). The concentrate was dried using a Niro spray dryer (model SD-6.3N, GEA). The liquid was atomized by means of a bifluid nozzle and the inlet air temperature entered the drying chamber at 140° C. The enzymatic treatments and addition of sunflower after UHT treatment were strategies to decrease the viscosity in order to allow a more efficient spray drying process.

Viscosity:

The viscosity was measured in a modular compact rheometer (Anton PAAR, Graz) with a concentrical cylinder system at a temperature of 60° C.

Results:

100 l/s: 193±0 maP*s 600 l/s: 65±0 maP*s

TS limit for spray drying at 60° C.: 28.8%

Particle Size:

Wet method: Particle size dispersed in water was measured with a Mastersizer 2000 (Malvern instruments Ltd., United Kingdom), using laser diffraction. Samples were dispersed in a Hydro 2000 G water dispersion unit (Malvern instruments Ltd., United Kingdom) at room temperature. Characteristic particle size $d_{10}$, $d_{50}$ and $d_{90}$ are calculated from normalized curves, corresponding to the particle size of 10%, 50% and 90% of the particles respectively.

Dry Method:

Particle size of powders was measured by Camsizer XT (Retsch Technology GmbH, Germany). The technique of digital image analysis is based on the computer processing of a large number of sample's pictures taken at a frame rate of 277 images/seconds by two different cameras, simultaneously. Characteristic particle size $d_{10}$, $d_{50}$ and $d_{90}$ are calculated from normalized curves, corresponding to the particle size of 10%, 50% and 90% of the particles respectively.

| Particle size | D10 [µm] | D50 [µm] | D90 [µm] | D4,3 [µm] |
|---|---|---|---|---|
| Wet; before drying | 2.1 | 36.0 | 139.0 | 103.0 |
| Dry, Powder | 14.3 | 50.2 | 247.9 | 95.7 |

Example 14: Beverage Comprising Chickpea, Sunflower, and Oat Powder with Amylase and Glucosidase Treatment Obtained at Pilot Plant Scale Chickpeas were sourced from Vivien Paille (France). Chickpea de-hulling was carried out using shelling Machine (F.H. SCHULE Mühlenbau GmbH, Germany) for 100 s and at 90% of maximum speed. The chickpeas were then roasted using a Salvid combisteam CSC furnace (Germany) operating at 160° C. for 40 minutes. 45% chickpea was mixed with 35 wt % (partially) defatted sunflower flour (Heliaflor 45, Austrade, Germany) and 20% oat grains. The premix was treated in a hammer milling (Retsch ZM1, Switzerland) operating at speed 2 with 12 knifes and grid size of 0.5 mm in order to produce a homogeneous premix. 12% of the obtained mixture was mixed with 88% of water. The dispersion was then introduced into a Tetra Almix B200-100 VA Scanima reactor (Germany). The mixture was heated under agitation for 15 minutes at 90° C., followed by cooling down to 80° C. 0.003 wt %, in reference to the total mass, of Ban 800 (Novozymes, Denmark) which contains the enzyme alpha amylase as active component was added. The temperature was kept at 80° C. and agitation was carried out for 15 minutes. After cooling the mixture to 65° C., 0.04 wt %, in reference to the total mass, of AMG300 (Novozymes, Denmark) with amyloglucosidase as active component was added. The enzymatic treatment was carried out under agitation at 65° C. for 1 hour. For further refining, the obtained dispersion was passed through a colloidal mill (Process pilot 2000-4 IKA-Werke in Colloidal milling configuration) having a gap of 50 microns and two homogenization passes (APV, HTST, Germany) using pressure of 300/50 Bars. For enzyme inactivation the dispersion was treated by ultra high temperature using a temperature of 143° C. for 5 seconds (APV, HTST, Germany). In order to obtain a powder the dispersion was dried using a Niro spray dryer (model SD-6.3N, GEA). The liquid was atomized by means of a bifluid nozzle and the inlet air temperature entered the drying chamber at 140° C.

Viscosity:

The viscosity was measured in a modular compact rheometer (Anton PAAR, Graz) with a concentrical cylinder system at a temperature of 60° C.

Results:

100 l/s: 217.4±16.4 maP*s
600 l/s: 114.2±5.8 maP*s
TS limit for spray drying at 60° C.: 24.9 mPas

| Particle size | D10 [μm] | D50 [μm] | D90 [μm] | D4,3 [μm] |
|---|---|---|---|---|
| Wet; before drying | | 24 | 85 | 37 |
| Dry, Powder | 8.5 | 24.8 | 59 | 42 |

The invention claimed is:

1. A liquid vegan food composition comprising at least 5 wt % cereal on a dry basis and at least 10 wt % legume on a dry basis, wherein the composition comprises at least 2 wt % dietary fiber provided by the cereal and the legume and at least 5 wt % protein provided by any one or more of the cereal and the legume, and wherein a D4,3 particle size of the composition is less than 100 microns.

2. The liquid vegan food composition according to claim 1, wherein the composition comprises between 15 to 50 wt % cereal on a dry basis, and between 50 to 85 wt % legume on a dry basis, wherein the composition comprises between 5 to 20 wt % dietary fiber provided by the cereal and the legume and between 5 to 40 wt % protein provided by any one or more of the cereal and the legume.

3. The liquid vegan food composition according to claim 1, wherein the composition is a milk analogue.

4. The liquid vegan food composition according to claim 1, comprising between 30 wt % and 50 wt % cereal on a dry basis, and between 50 wt % to 70 wt % legume on a dry basis.

5. The liquid vegan food composition according to claim 1, wherein the cereal is oat or quinoa.

6. The liquid vegan food composition according to claim 1, wherein the legume is chickpea or lentil.

7. The liquid vegan food composition according to claim 1, comprising between 13 wt % and 38 wt % protein on a dry basis provided by the cereal and legume.

8. The liquid vegan food composition according to claim 1, further comprising oilseed selected from the group consisting of sunflower, pumpkin seed, egusi seed, rapeseed, cotton seed, grapeseed, chia seed, flaxseed, Tamarin seeds, sacha inchi seed, moringa seed, marama seeds, locust bean seeds, melon seeds, watermelon seeds, cucurbit seeds, Okra seeds, Ochro seeds, cacti seeds, cactus seeds, papaya seeds, shea nut, hemp seeds, safflower seeds, and canola seeds.

9. The liquid vegan food composition according to claim 8, wherein the liquid vegan food composition comprises between 25 wt % to 50 wt % oilseeds on a dry basis.

10. The liquid vegan food composition according to claim 1, wherein the D4,3 particle size of the composition is less than 75 microns.

11. The liquid vegan food composition according to claim 1, wherein said cereal and the legume are provided as a powder or a flour which is not a protein isolate or protein concentrate.

12. The liquid vegan food composition according to claim 1, wherein a fat content of the liquid vegan food composition is between 5-15 wt %.

13. The liquid vegan food composition according to claim 1, wherein an amino acid score of the liquid vegan food composition is higher than 0.7.

14. The liquid vegan food composition according to claim 1, wherein a ratio of total lysine in mg to total protein in g of the liquid vegan food composition is higher than 30.

* * * * *